United States Patent
Franetzki

[19]
[11] Patent Number: 5,807,521
[45] Date of Patent: Sep. 15, 1998

[54] METHOD AND APPARATUS FOR CLEANING AND STERILIZING A DENTAL APPARATUS

[75] Inventor: Manfred Franetzki, Bensheim, Germany

[73] Assignee: Siemens Aktiengesellschaft, Munich, Germany

[21] Appl. No.: 556,562

[22] Filed: Nov. 13, 1995

[30] Foreign Application Priority Data

Nov. 14, 1994 [EP] European Pat. Off. .............. 94117949

[51] Int. Cl.$^6$ ..................................................... A61L 2/02
[52] U.S. Cl. ................................ 422/20; 422/21; 422/24; 422/28; 422/128; 422/300
[58] Field of Search ................................ 422/20, 21, 24, 422/28, 127, 128, 300

[56] References Cited

U.S. PATENT DOCUMENTS

| | | | |
|---|---|---|---|
| 3,837,805 | 9/1974 | Boucher | 422/128 |
| 4,191,291 | 3/1980 | Brown | 422/297 |
| 4,448,750 | 5/1984 | Fuesting | 422/20 |
| 4,545,956 | 10/1985 | Ciszewski et al. | 422/28 |
| 5,197,499 | 3/1993 | Bodenmiller et al. | 422/116 |
| 5,225,160 | 7/1993 | Sanford et al. | 422/28 |
| 5,447,684 | 9/1995 | Williams | 422/20 |
| 5,480,302 | 1/1996 | Fife | 422/20 |
| 5,547,635 | 8/1996 | Duthe, Jr. | 422/22 |

FOREIGN PATENT DOCUMENTS

| | | |
|---|---|---|
| 0 111 249 | 2/1986 | European Pat. Off. . |
| 0 403 442 | 12/1990 | European Pat. Off. . |
| 2 627 086 | 4/1989 | France . |
| 28 05 934 | 8/1978 | Germany . |
| 34 40 078 | 1/1991 | Germany . |

*Primary Examiner*—Thomas G. Wyse
*Attorney, Agent, or Firm*—Hill, Steadman & Simpson

[57] ABSTRACT

A method and apparatus for cleaning and sterilizing all parts of a dental apparatus head exposed to contamination in a practical and economical way includes a cleaning chamber, which may be either a separate unit or an integral part of an apparatus head which receives dental instruments connected by hoses to the head. In one embodiment, the chambers are formed within the head and is closed by a flexible cover so that a cleaning fluid can be introduced into the chamber to clean the exterior surfaces and then disinfectants can be sprayed on the exterior surfaces and pass through internal conduits of the hoses and instruments. In another embodiment, the chamber is separate and receives the entire apparatus head and/or support brackets and is closable so that the head and/or support brackets can be thoroughly cleaned on the external surfaces and then subsequently disinfected with the internal surfaces being disinfected.

20 Claims, 10 Drawing Sheets

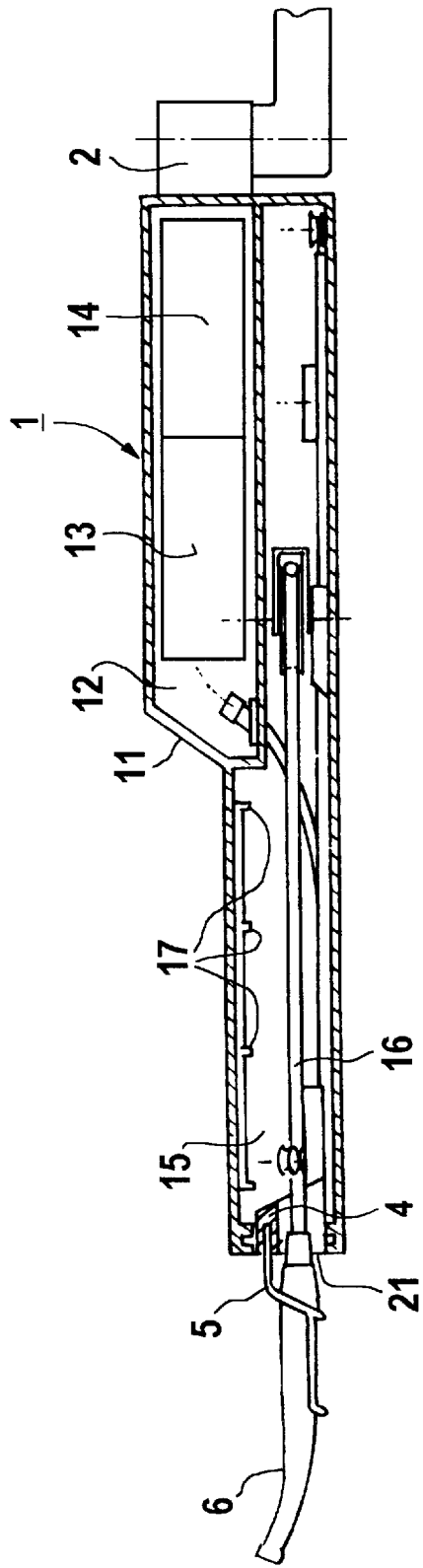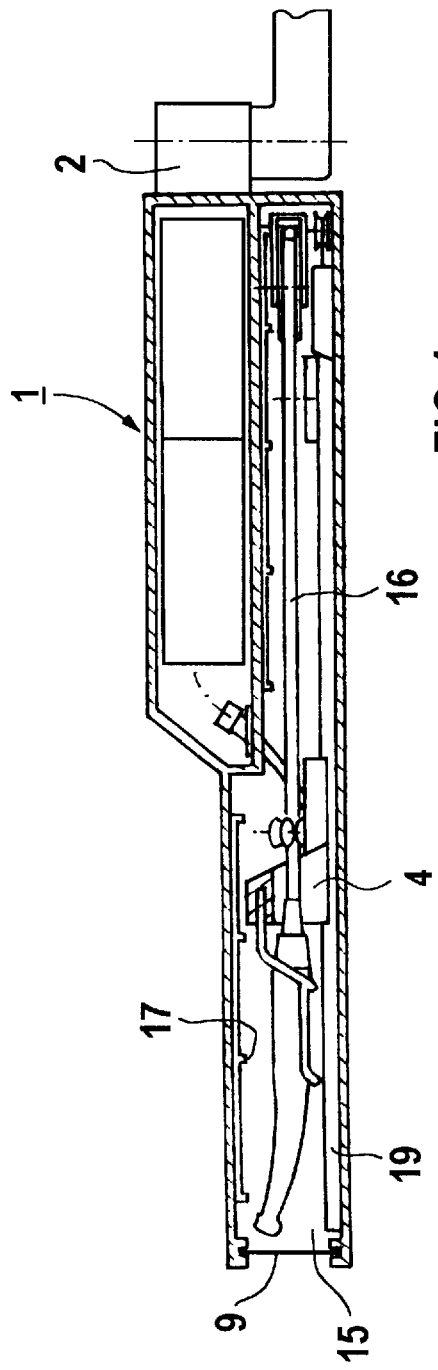

METHOD AND APPARATUS FOR CLEANING AND STERILIZING A DENTAL APPARATUS

BACKGROUND OF THE INVENTION

The present invention is directed to a method of cleaning and sterilizing a dental apparatus head or tray, which encompasses deposit holders for hose-connected instruments, also contains operating fields and is equipped with a manipulator with which the head or tray can be positioned in different treatment positions. The invention is also directed to an apparatus for the implementation of the method.

There is a risk in dental treatment of transmitting germs in essentially three ways:

Given preparations in the patient's mouth, particles contaminated with germs can be discharged from the patient's mouth by the spray employed when cooling the preparation area. Thus, the attending personnel can be directly contaminated with germs as a result of the spray. The personnel can protect themselves against the transmission of germs by basic suitable measures, such as utilizing goggles and masks.

Germs can proceed into the supply channels via the water main or via the treatment instruments and multiply therein. These germs can be killed with biocidal additives in the supply agents. A method suitable for this is disclosed, for example, in U.S. Pat. No. 4,545,956, whose disclosure is incorporated by reference thereto and which claims priority from the same German Application as European Published Application 0 111 249.

Germs can be suctioned or drawn back into agent channels. The suctioning of germs back into the agent channels of the instrument or, respectively, delivery conduits can, in fact, be largely prevented with valves arranged at suitable locations and a recontamination of the instruments can be prevented by sterilization. For sterilizing instruments, the instruments must usually be uncoupled, first from the supply hoses and then be separately treated in a sterilizer or disinfector.

The sterilization of those parts of a dental apparatus head or equipment tray which are necessarily touched by attending personnel, potentially also by the patient, and are, thus, especially highly exposed to bacterial contamination and cannot be introduced into currently-standard disinfectant or, respectively, sterilization apparatus, represents a major problem. Included among those, in particular, are grips, operating fields or other housing parts that are currently usually treated only with a disinfectant spray. This is also basically true of instrument holders or, respectively, instrument deposits or trays.

German Patent 34 40 078 discloses a dental unit having a sterilizable apparatus part, wherein the apparatus head can be sterilized from the outside by ultraviolet light or with the assistance of a dry gas. The apparatus head with the instrument is introduced into a shaft which is suspended from the ceiling of the room. In the engaged condition, the shaft can be closed by a cover adjacent its lower opening. The following treatment is exclusively limited to a dry sterilization of the external parts where no cleaning and, thus, no sterilization of the inner parts will occur.

The goal of a comprehensive sterilization of all parts coming into contact with germs can, thus, not be achieved with the known means and cannot be economically justified with the above-described methods. In practice, the result is that a consistent sterilization is usually foregone.

SUMMARY OF THE INVENTION

The present invention is directed to an object of providing a method for cleaning and sterilizing with a designational cleaning and sterilizing of both the agent channels as well as other, especially exterior parts, and to an apparatus which will allow the implementation of this method in a practical and economically feasible way.

To accomplish this goal, the method for cleaning and sterilizing a dental apparatus head or tray which has deposit holders for instruments connected to hoses and contains an operating field is equipped with a manipulator with which the head or tray can be positioned in different treatment positions comprises the steps of introducing the instruments together with their hoses, which are still connected thereto, the manipulators and the operating fields as well into a closable disinfector chamber, then cleaning the outside of the parts by jet-blasting with a cleaning agent or utilizing an ultrasound bath and then disinfecting the exterior surfaces as well as the delivery lines in the hoses and channels of the instrument with a disinfectant.

According to the invention, all parts coming directly or indirectly into contact with the germs are automatically cleaned and subsequently sterilized in situ, i.e., without prior disassembly of the parts, and while in the operating condition. The cleaning occurs in that the exterior surfaces are blasted with the assistance of a pressurized cleaning agent. This can advantageously occur with a water jet or a steam jet or in an ultrasound bath. It is also conceivable and within the scope of the invention to employ other suitable cleaning agents. The delivery of the cleaning agents advantageously occurs via a nozzle system having a plurality of nozzles that are arranged in a closable disinfector chamber. The sterilization of the delivery conduits and the channels in the instruments can occur according to the known method initially set forth.

The sterilization of the external surfaces can occur with a suitable means, for example by spraying with a biocidal chemical, with $H_2O_2$, with steam or by flooding with ozonated water. Flooding with ozone gas, hot air or other biocidal gasses or an irradiation with ultraviolet light, microwave radiation or irradiation with ultrasound is also conceivable.

According to an advantageous embodiment, it is not only instruments connected by hoses, operating fields and manipulators that are subjected to the cleaning and sterilization method but, at the same time, even additional parts attached to the apparatus head or tray, particularly an instrument deposit tablet or tray, potentially including the instruments lying thereon and/or an expectoration basin that are co-treated.

The apparatus includes forming a disinfector chamber, which may be part of the apparatus head or a separate chamber which receives the apparatus head. The chamber is provided with a cover means for closing the chamber and with a nozzle system for delivering the cleaning agent.

Other advantages and features of the invention will be readily apparent from the following description of the preferred embodiments, the drawings and claims.

BRIEF DESCRIPTION OF THE DRAWINGS

FIG. 3 is a transverse cross sectional view of the apparatus of FIG. 1 in an opened or operating position;

FIG. 4 is a cross sectional view similar to FIG. 3 with the dental instruments in the retracted position and the apparatus closed to perform a cleaning and disinfecting operation;

DESCRIPTION OF THE PREFERRED EMBODIMENTS

Figure 1:
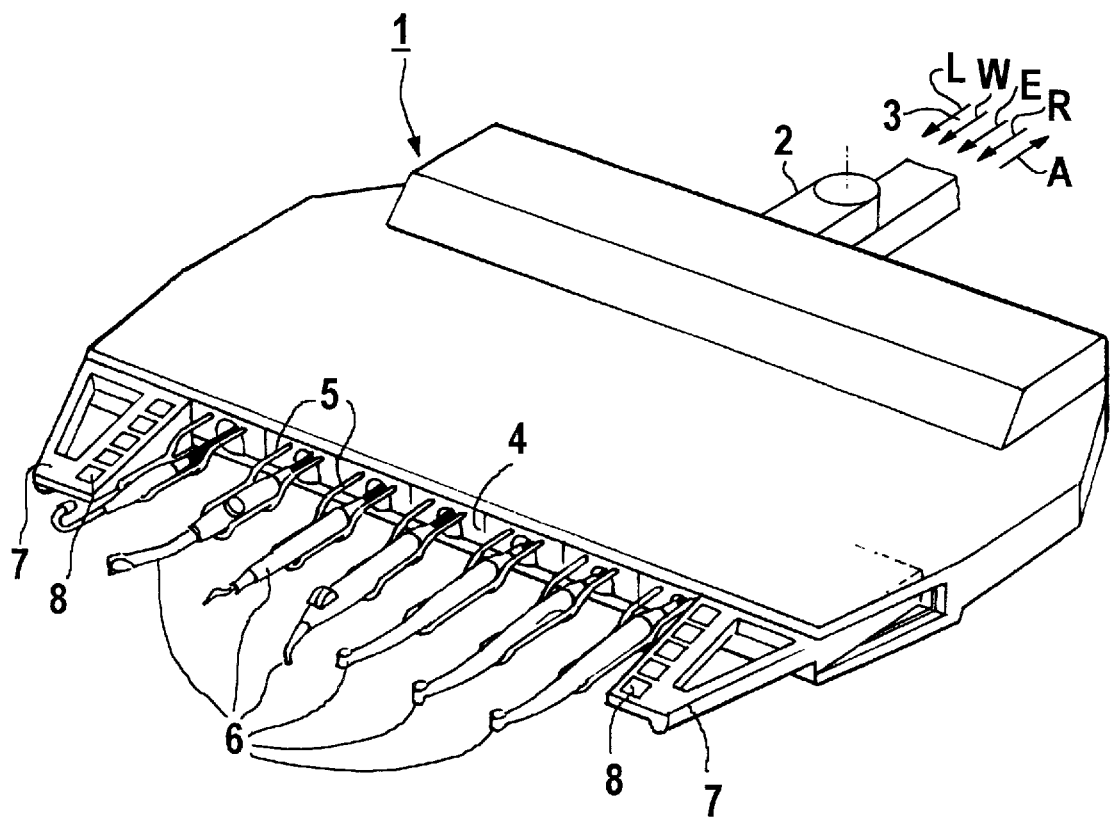
FIG. 1 is a perspective view of an apparatus head having holders and grips in an operating position.

The principles of the present invention are particularly useful when incorporated in a dental apparatus head, generally indicated at 1 in FIG. 1. The apparatus head 1 is mounted on a bracket 2, which is connected to either a floor stand or a wall mounting or ceiling adapter, and the bracket allows the apparatus head to be brought into various treatment positions relative to a patient. The bracket 2 contains delivery conduits for air, water and electrical energy, for cleaning agents, as well as a drain line for waste liquid or water. These conduits are indicated by arrows 3, with the arrow L being for air, the arrow W being for water, the arrow E being for electrical energy, the arrow R being for cleaning agents and the arrow A for waste water or liquid return. These conduits all proceed in the bracket 2 in a known manner.

Figure 2:
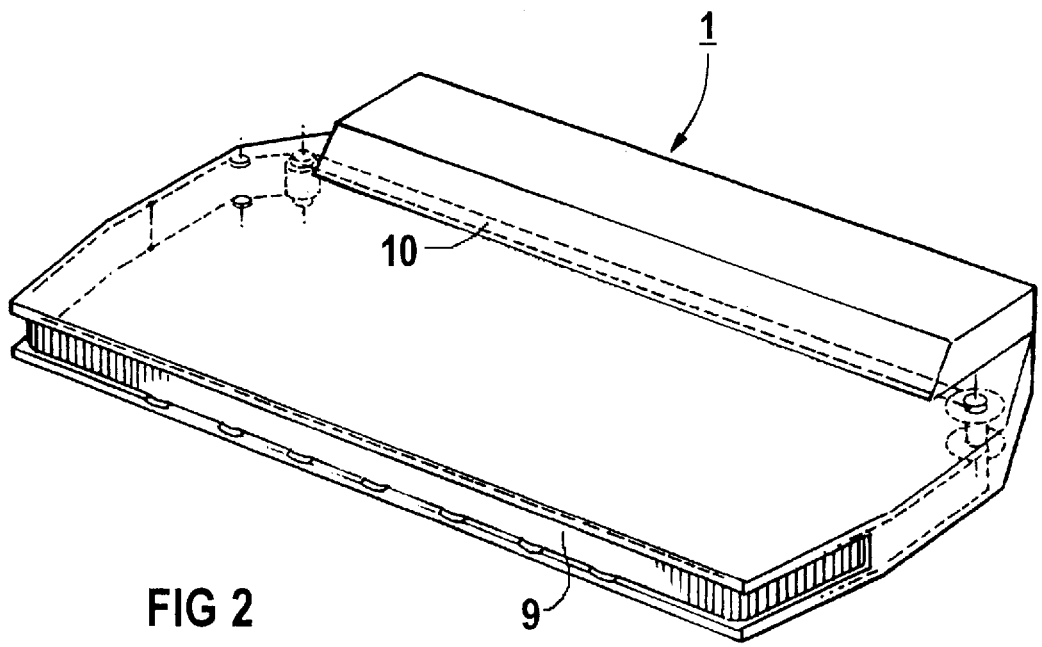
FIG. 2 is a perspective view of the apparatus head of FIG. 1 closed for cleaning and sanitizing the interior thereof.

The apparatus head 1 has a plurality of holder ledges or members 4, which have a plurality of deposit devices 5 for various instruments 6 which have hose connections extending into the head 1. In addition, grips or manipulators 7 are provided on the apparatus head 1 and contain integrated operating fields 8 disposed on both sides of the instrument arrangement. As described in greater detail below, the holder members 4 with the instruments can be retracted into the inside of the apparatus head 1. In addition, the two grips 7 with the integrated operating fields 8 can be pivoted toward the inside. In the non-use or retracted position, the remaining opening of the head 1 is covered by a movable blind or band 9 (see FIG. 2), which can be moved with a cable pull 10 from a released or opened position illustrated in FIG. 1 to a position for closing the opening 21, as best illustrated in FIGS. 2 and 4. By releasing the band or blind 9, the slot-like opening 21, as illustrated in FIG. 3, will be open to allow the emergence of the various holder members 4 with their respective instruments and the grips 7. As illustrated in FIG. 2, the opening is tightly closed by the band in a non-use position, which is also a position for cleaning and sterilizing the parts disposed inside of the head.

As best illustrated in FIGS. 3 and 4, the apparatus head 1 has a housing 11 which comprises an upper holding position 12 in which electronic controls 13, as well as a mechanical system 14 which includes valves, are arranged. Since these parts are not critical for the present invention, they are illustrated in block diagram and include the control valves necessary for the method described in greater detail below and with which, on the one hand, the inflow of the agents to the instruments and, on the other hand, the delivery of cleaning agents as well as the elimination of waste or wash water can be controlled.

A lower retaining portion 15 is free of the housing 11 and is free of electrical and electronic component parts and merely contains an admission for a cleaning agent as well as an outlet for waste water. In the illustrated embodiment, this lower retaining portion or hole 15 forms a disinfector chamber in which, when the instruments 6 and the supply hoses 16 are retracted and when the grips 7 are folded in, these parts are subjected to an automatic cleaning and disinfection. To this end, a nozzle arrangement 17 that is connected to a feeder for cleaning agents R is located in a front part of the disinfector chamber 15.

Figure 5:
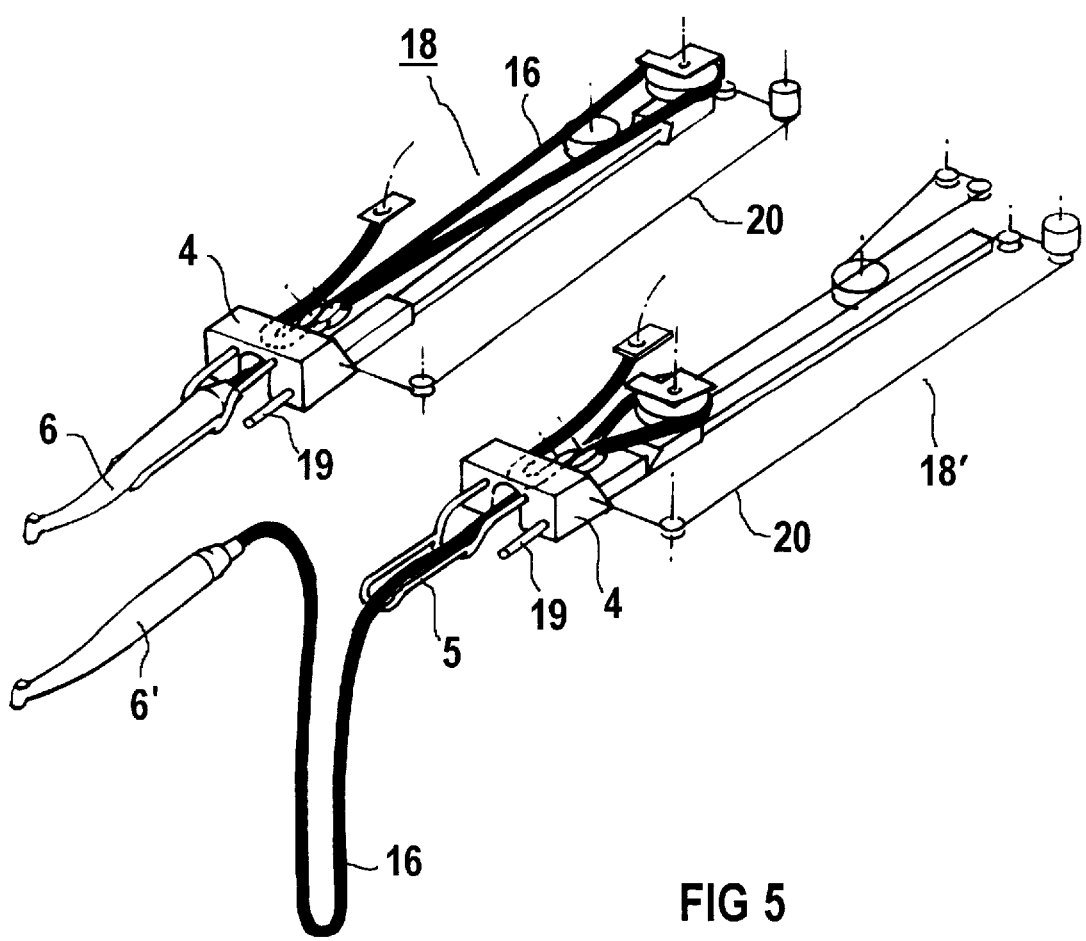
FIG. 5 is a perspective view of two dental instruments of the device of FIG. 1, with one in a stored position and the second in an operating position illustrating the take-up arrangement for the hose connected to the instrument.

As schematically illustrated in FIG. 5, the structure of the hose train 18 is illustrated. In the upper portion of FIG. 5, the instrument 6 is in the holder and the hose 16 is in a retracted position. In the lower portion of FIG. 5, the instrument 6' has been removed from the holder 5 and the hose train 18' is in the advanced position to provide slack in the hose 16 to enable manipulation of the instrument 6'. The actual proposed structure of the hose trains 18 and 18' are known in the art. The member or block 4 for the holder 5 is movable along guide rods 19, which are secured in the disinfector chamber 15. This can be accomplished by utilizing a motor-driven cable pull 20 which will shift the holder 5 and the block 4 from the advanced position illustrated in FIG. 5 to a retracted position within the chamber 15, as illustrated in FIG. 4.

The holder member or block 4 can be fashioned as one piece so that all instruments are simultaneously retracted and can be moved or placed in the operating position. However, each of the holder members 4 can be fashioned as a multiple part, with a single holder member 4 being provided for each instrument, and these members are capable of being retracted or extended into the outlet position independently of one another.

The cleaning and sterilizing procedure sequence is as follows:

After the instruments, such as 6, and the two grips 7 with the operating fields 8 have been retracted into the disinfector chamber 15, the remaining opening 21 is closed with the blind or band 9. After this, the cleaning agent in the form of pressurized water or steam is introduced by the nozzle system 17. The arrangement of nozzles is thus undertaken so that the instruments together with the hose connected thereto and the two grips 7 with the operating fields are first spray-blasted on the outside. After the wash water has been pumped out, the exterior surfaces are subsequently charged with a disinfectant. At the same time, a disinfectant flow is forced through the delivery conduits in the hoses as well as the channels of the instruments from the interior. To this end, the delivery of spray water to the instruments is interrupted in the valve block 14 and the disinfectant is conveyed instead to the instruments. The residual moisture present in the disinfector chamber after the wash water has been pumped out can be removed by creating an air flow by blowing warm air into the chamber or by extracting the air therefrom.

Ozone can be added to the water for intensifying the disinfecting effect. In addition, the cleaning effect can likewise be intensified by utilizing ultrasound in that an ultrasound generator is placed at a suitable location in the chamber 15 and the instrument lie in a liquid bath which is subjected to the ultrasound radiation.

Figure 6:
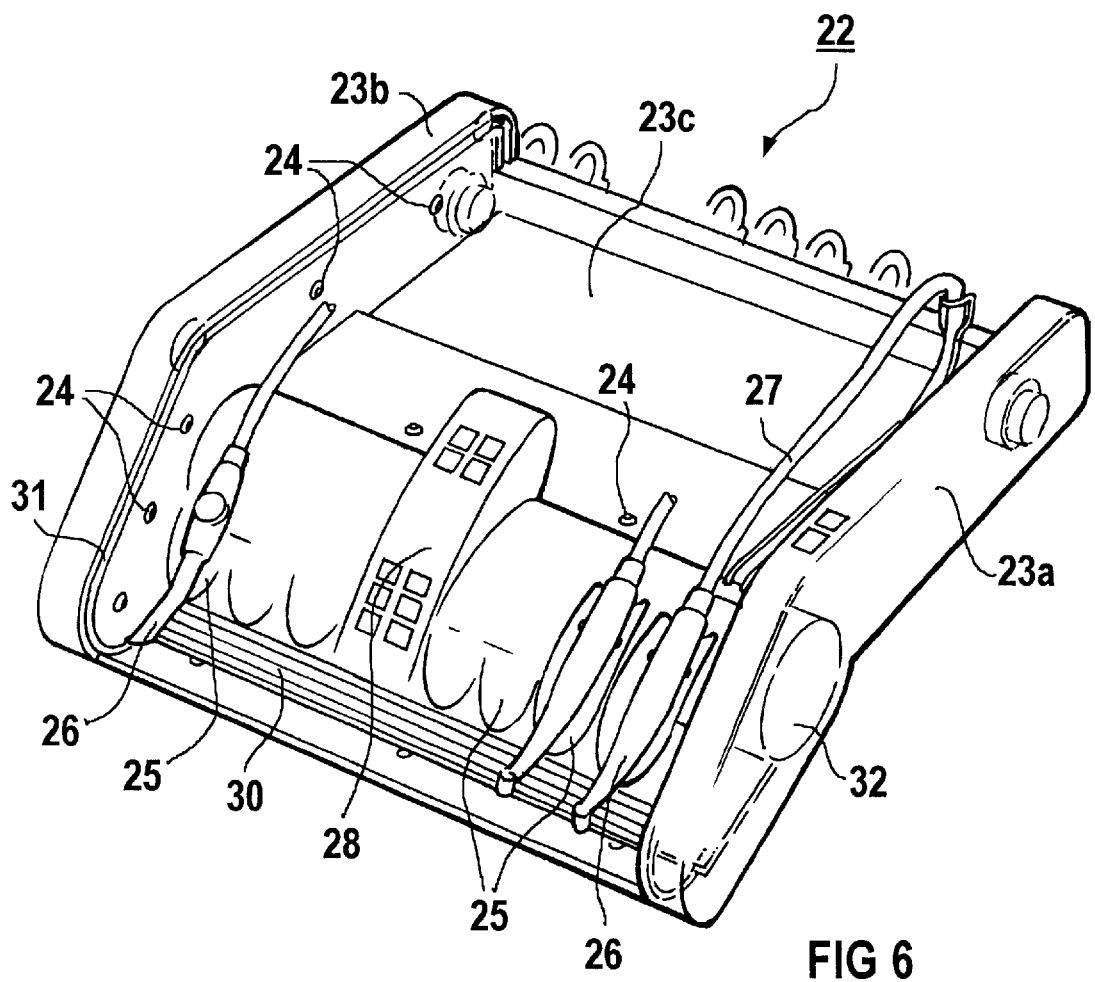
FIG. 6 is a perspective view of a second embodiment of a dental apparatus having a closable chamber for cleaning and disinfecting dental instruments.
Figure 7:
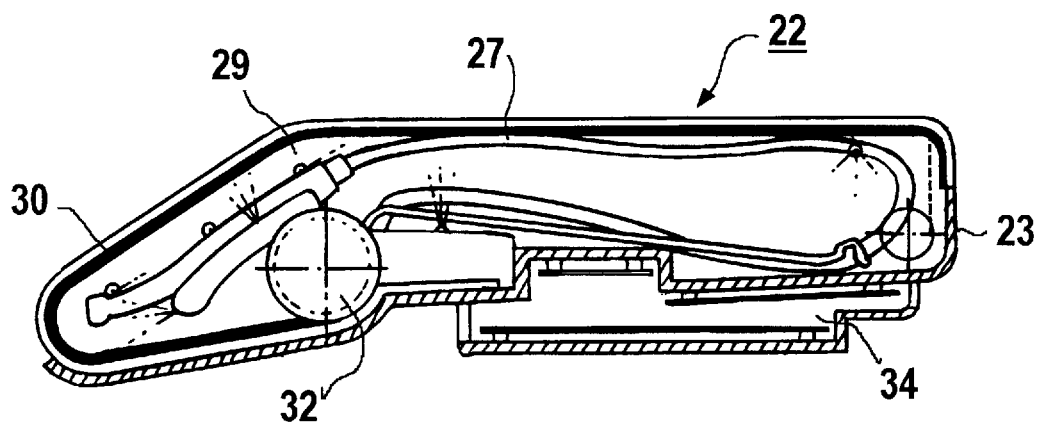
FIG. 7 is a cross sectional view of the embodiment of FIG. 6 with the chamber being closed.

In a second embodiment illustrated in FIGS. 6 and 7, the method for cleaning and disinfection proceeds in a similar way. The differences compared to the preceding example are in the structural format of the differently-fashioned apparatus head.

In the embodiment of FIGS. 6 and 7, the apparatus head 22 contains a housing 23 fashioned tank-like. Nozzles 24 for the delivery of cleaning agent are arranged in the two side walls 23a and 23b and the floor 23c. The apparatus head 22 further includes deposit holders 25 for the instruments 26 and their hoses 27 that are removed and deposited in the fashion of a whip. An operating field, such as 28, is integrated in the carrier of the deposit holder 25. Here, the disinfector chamber 29 is formed, on the one hand, by the housing 23 and, on the other hand, by a blind or flexible cover 30 that closes the tank and covers the instruments in their deposited condition. The blind or cover 30 is guided in lateral guides 31 and can be retracted and extended by a motor having a driven drum 32. As indicated in the cross sectional view of FIG. 7, the electronic and electrical component parts are accommodated in a separate retaining chamber or space 34 under the housing 23.

Figure 8:
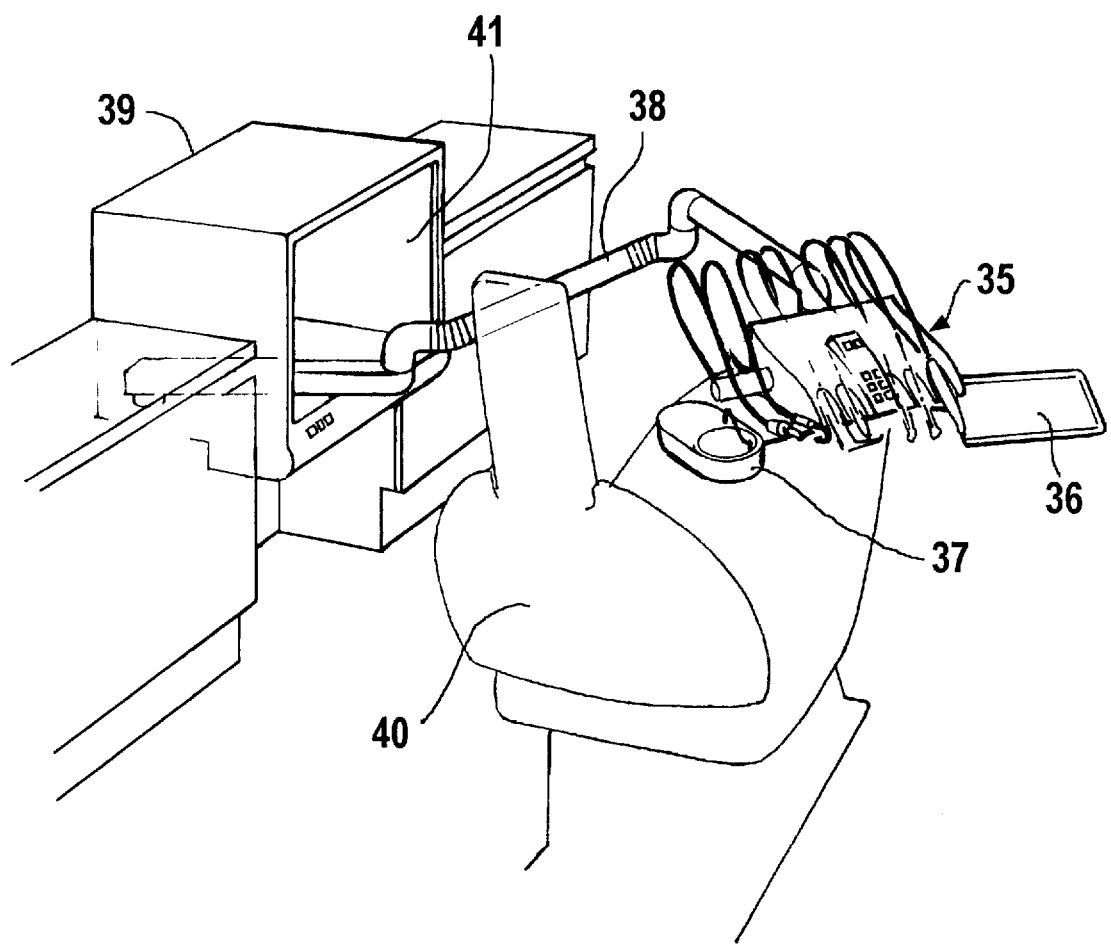
FIG. 8 is a perspective view of a third embodiment of a chamber for cleaning and sterilizing an apparatus head.
Figure 9:
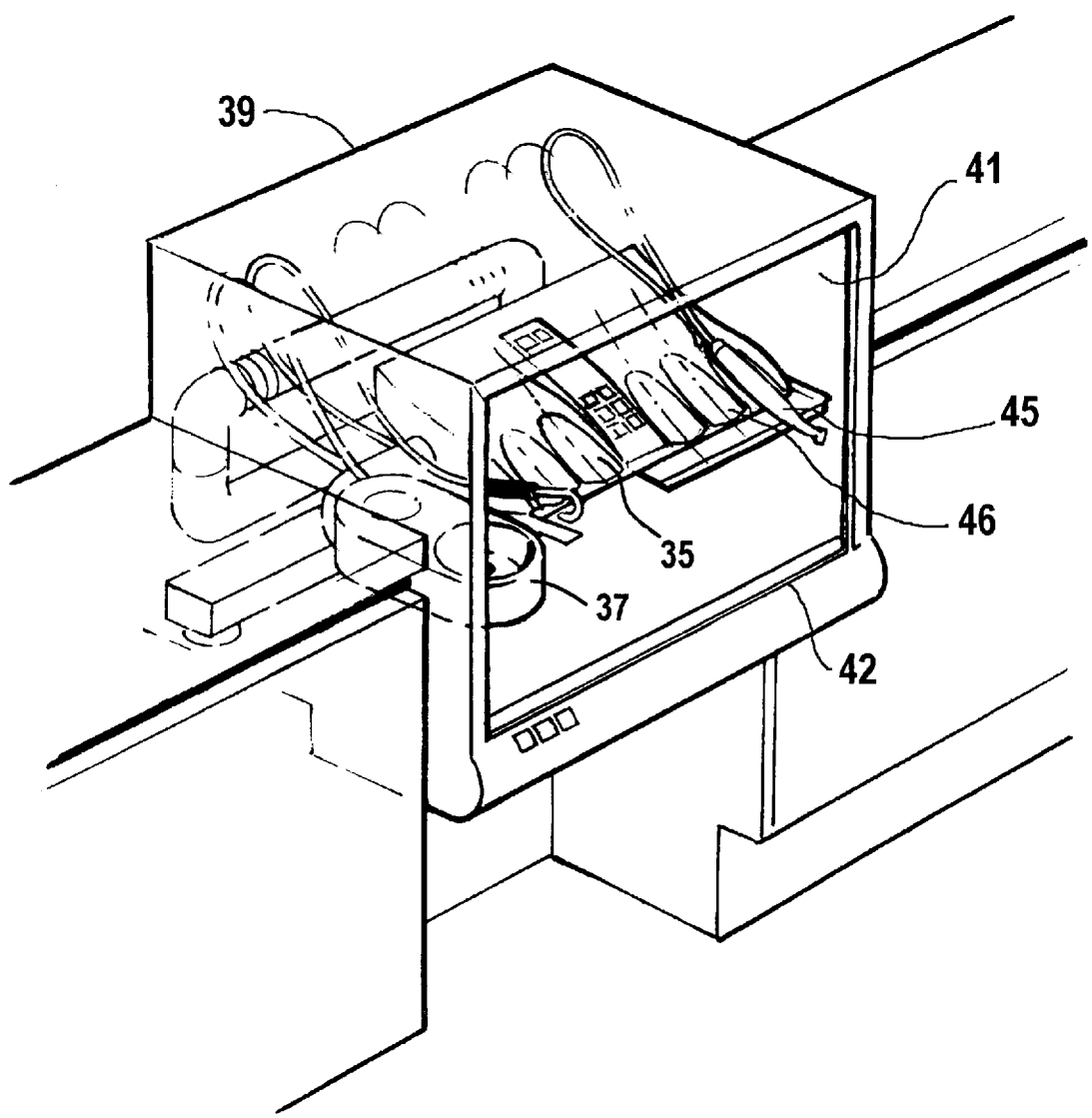
FIG. 9 is a perspective view with the dental head and apparatus disposed in the cleaning chamber.
Figure 10:
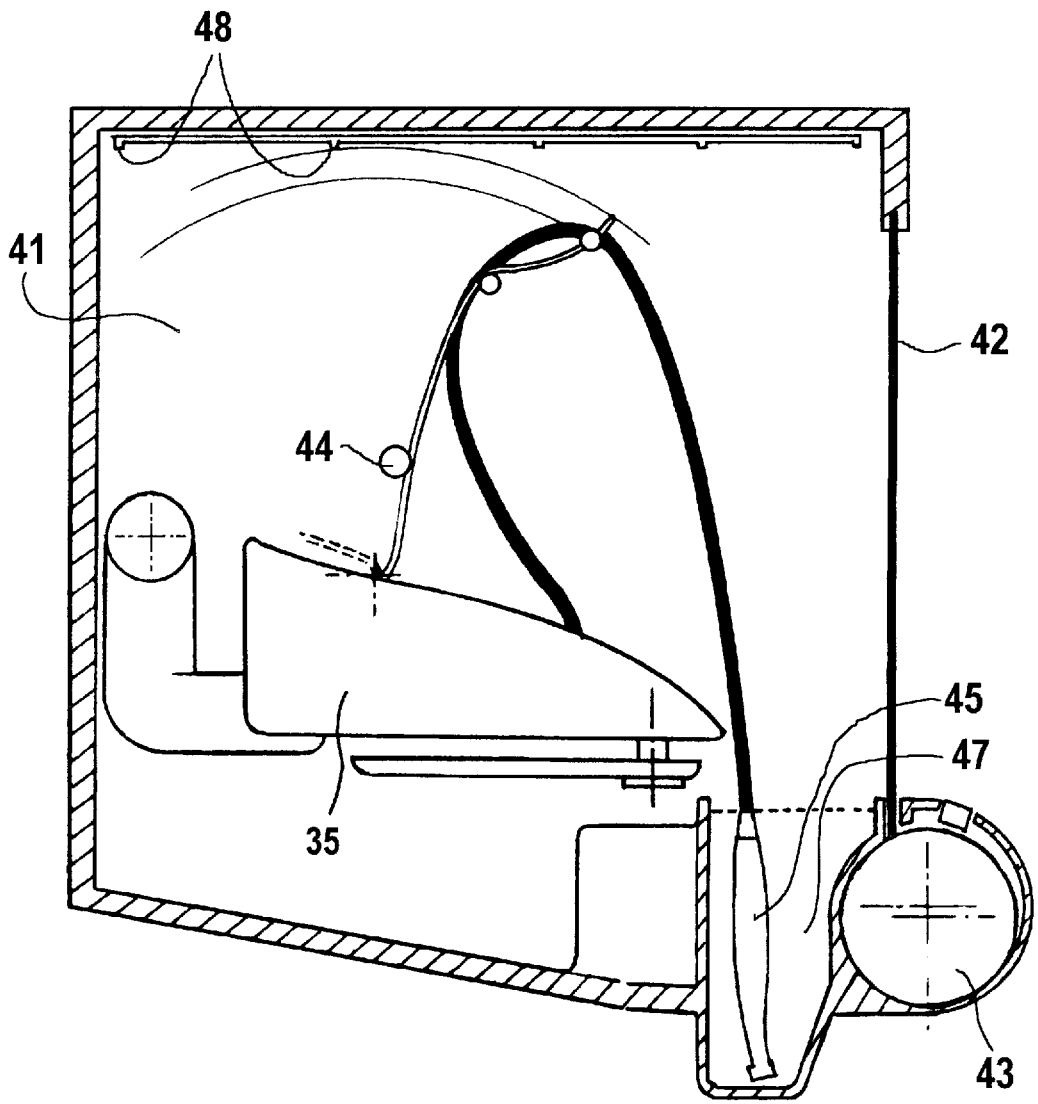
FIG. 10 is a cross sectional view with the cleaning chamber being closed illustrating the positions of the various parts of the apparatus during a cleaning operation.

A third embodiment is shown in FIGS. 8, 9 and 10 and have an apparatus head, generally indicated at 35, which has what is referred to as "whip holders" for the instruments, as explained above. By contrast to the embodiment that has already been described, this apparatus head 35 contains two additional elements, namely a tray 36 and an expectoration basin 37. In addition, the head 35 is carried by a multi-element bracket 38, whose other end is mounted inside a box-like built-in cabinet 39 which is positioned laterally next to or at the foot of the patient chair 40. The interior 41 of the box-like cabinet 39 forms a disinfector chamber into which not only the apparatus head 35 together with the instrument tray 36 and expectoration basin 37 but also the entire bracket 38 can be retracted (see FIG. 9). A blind or flexible cover 42 can be wound from a drum 43 (FIG. 10) situated under the introduction opening for covering a front side and closing the opening. The closure of the chamber, however, can also occur in various other ways.

As illustrated in FIG. 10, what is referred to as a "whip guard" in the form of a rod 44 is located in the disinfector chamber 41. This guard 44 sees to it that the whips are erected after insertion of the apparatus head 35 into the disinfector chamber. The instruments 45 are thereby lifted from their tray or holder 46 (see FIG. 9) and immersed into a tank-like depression 47 located in the chamber. The depression 47 can be filled with a cleaning fluid and can be potentially equipped with a device for emitting ultrasound irradiation. A specific washing means can also be arranged therein so that the instruments are treated therein with a water or steam jet.

As in the previously-described embodiments, various nozzles 48 are provided in various positions in the housing. The cleaning fluid for the exterior cleaning of the parts can be directed onto the parts by these nozzles 48.

It should be pointed out at this juncture that the embodiment that has been described can also be viewed in combination with a structure according to FIGS. 6 and 7. For example, a possibility also is provided in that embodiment for the automatic immersing of the instruments, in their deposited condition, into a corresponding provided tank in which cleaning fluid is located.

Figure 11:
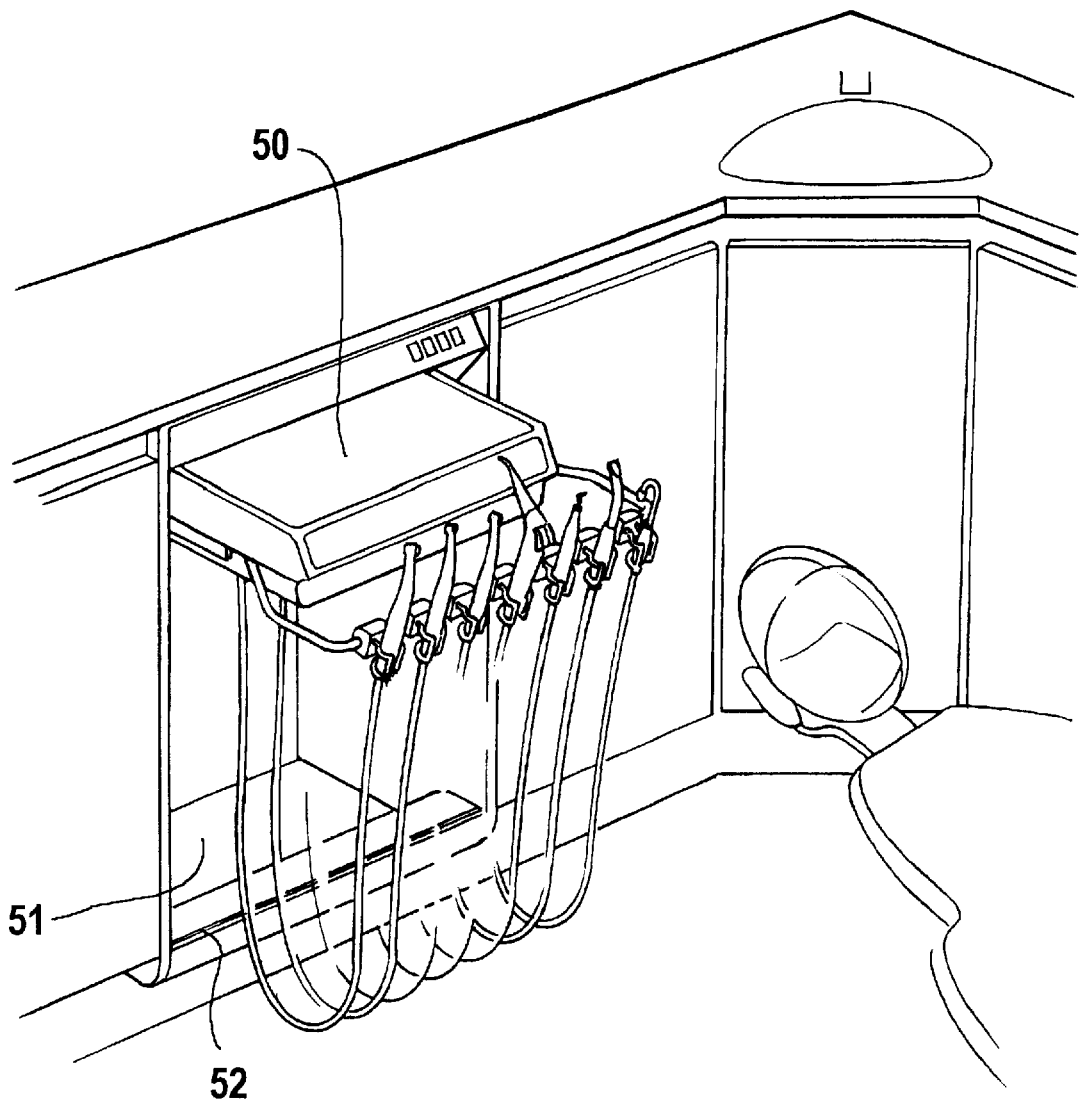
FIG. 11 is a perspective view of a fourth embodiment of an apparatus for cleaning and disinfecting a dental instrument and apparatus head for the instrument.
Figure 12:
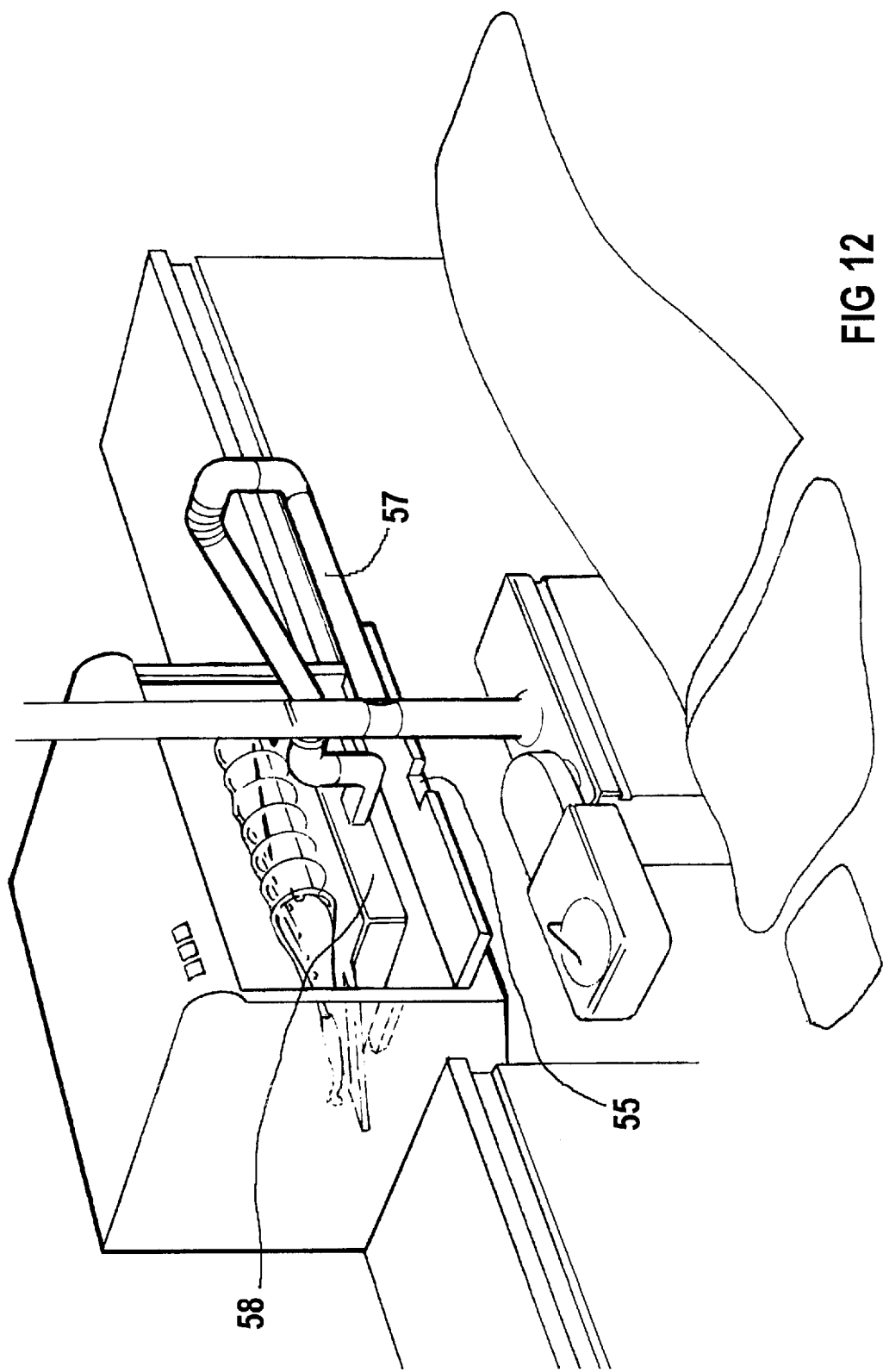
FIG. 12 is a perspective view of a fifth embodiment of the cleaning and disinfecting apparatus.
Figure 13:
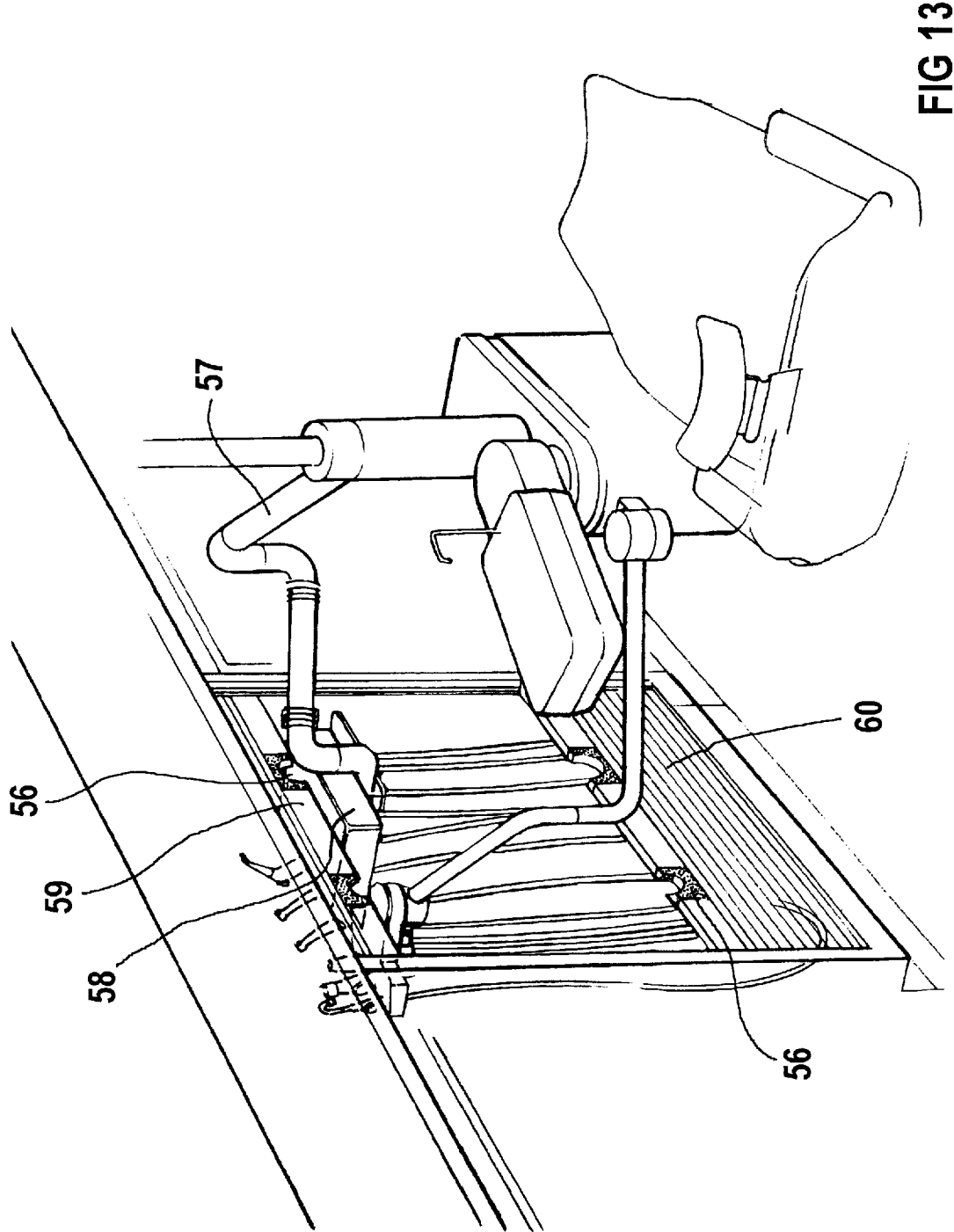
FIG. 13 is a perspective view of a sixth embodiment of the cleaning and disinfecting apparatus.

Three additional disinfector chambers are illustrated in FIGS. 11, 12 and 13. In each of these chambers, an apparatus head, such as 50 in the embodiment of FIG. 11, is introduced into a cabinet-like disinfector chamber 51 and this chamber is then closed with a flexible blind or band 52 or some other door. In the embodiments of FIGS. 12 and 13, only the apparatus head 58 is inserted into the chamber. The mount or bracket 57 on which the apparatus head 58 is secured, respectively, project laterally from the disinfector chamber. Appropriately-fashioned cutouts, such as 55, are provided in the partitions or housing parts 59 and 60 for closing the opening and the cutouts 55 may be provided with appropriate seals 56 in the blinds or housing parts 59 and 60, which form a door or closure for the opening of the cleaning chamber, to from a fluid-tight seal around the portion of the bracket extending from the chamber.

Although various minor modifications may be suggested by those versed in the art, it should be understood that I wish to embody within the scope of the patent granted hereon all such modifications as reasonably and properly come within the scope of my contribution to the art.

I claim:

1. A method for cleaning and sterilizing a dental apparatus that have instruments connected by hoses to the apparatus and have deposit holders for receiving the instruments, said dental apparatus including operating fields and being provided with a manipulator for positioning the apparatus in different treatment positions, the method comprising the steps of at least placing the instruments together with the attached hoses, the manipulator and operating fields in a closable disinfector chamber without disassembling the parts, cleaning the exterior surfaces of the dental instruments, the hoses, manipulators and operating fields by applying a cleaning agent selectively by jet-blasting and by utilizing an ultrasound bath, subsequently disinfecting the cleaned external surfaces and disinfecting internal channels of the hoses and instruments by forcing a disinfectant therethrough.

2. A method according to claim 1, wherein the disinfecting of the external surfaces of the parts together with the disinfecting of the internal channels of the hoses and instruments occurs in a single process.

3. A method according to claim 1, which includes inserting the dental apparatus into the disinfector chamber with the instruments, hoses, manipulators and operating field.

4. A method according to claim 1, wherein placing the hoses and instruments in a disinfector chamber creates the chamber within the dental apparatus.

5. A method according to claim 1, wherein the step of cleaning includes utilizing a cleaning fluid selected from pressurized water and steam jets, said step including projecting the stream with high-energy by nozzles onto the external surface of any parts to be cleaned.

6. A method according to claim 1, wherein the step of disinfecting uses an agent selected from hot air, steam, ozone water, gas, chemicals, ultraviolet light and microwave radiation.

7. A method according to claim 1, which includes immersing highly-contaminated parts, including the instruments, in a cleaning fluid during the step of cleaning, preferably between the steps of cleaning and disinfecting.

8. A method according to claim 7, wherein the step of immersing in a cleaning fluid includes immersing in an ultrasound bath.

9. A method according to claim 1, which includes removing moisture from the disinfector chamber by selecting a step of extracting air from the chamber or by blowing warm air into the chamber and then extracting the warm air therefrom.

10. An apparatus for cleaning and disinfecting a dental device having a head equipped with manipulators and having an operating field and hoses extending to instruments disposed in instrument deposit holders, said apparatus including a disinfector chamber being an integral component part of the apparatus head.

11. An apparatus according to claim 10, wherein the apparatus head is constructed as an instrument table having an operating side with a holder member with deposit holders for the instruments located therein, the apparatus head comprising a disinfector chamber into which at least the instruments together with their hoses can be introduced before the execution of the cleaning and disinfecting method, cover means for enclosing the chamber and a nozzle system being provided for delivering a cleaning agent being arranged in the disinfector chamber.

12. An apparatus according to claim 11, wherein the cover means includes a flexible blind that closes an introduction opening and is movable to a retracted position leaving the opening completely open.

13. An apparatus according to claim 12, wherein the cover means is a band movable between an opened and closed position by a cable pull.

14. An apparatus according to claim 11, wherein the holder member is held in the disinfector chamber with the assistance of a hose return means guided in a guide element.

15. An apparatus according to claim 10, wherein the disinfector chamber is formed by housing parts of the apparatus head and a covering therearound.

16. An apparatus according to claim 15, wherein the apparatus head is fashioned tank-like and a plurality of nozzles for the delivery of cleaning agents are arranged at least on lateral edge parts and on the floor of said tank.

17. An apparatus for cleaning a dental instrument head having holders for receiving instruments connected by hoses to said head, said apparatus including a separate disinfector chamber for receiving the apparatus head, said chamber having cover means for closing the chamber.

18. An apparatus according to claim 17, wherein the apparatus head includes whip-like instrument holders with instruments lying obliquely in a retracted position, said chamber including barrier means, said barrier means engaging said whip-like instrument holders to lift them into a raised position upon insertion of the apparatus head into the chamber with the instruments being immersed in a container located in the front of the chamber while the holders are in the raised position.

19. An apparatus according to claim 17, wherein the disinfector chamber is constructed so that at least the apparatus head and other parts, including a tray and expectoration basin, can be accommodated therein.

20. An apparatus according to claim 19, wherein the apparatus head is carried by a multi-element bracket secured to a base exterior of the disinfector chamber and the cover means for the chamber includes openings and seals for the bracket of said apparatus head so that when the apparatus head is placed in said chamber for cleaning, a seal is made on a portion of the bracket extending out of the chamber.

* * * * *